US010543046B2

(12) United States Patent
Charron et al.

(10) Patent No.: US 10,543,046 B2
(45) Date of Patent: Jan. 28, 2020

(54) DIGITALLY ENHANCED SURGICAL INSTRUMENTS

(71) Applicant: SYNAPTIVE MEDICAL INC., Toronto (CA)

(72) Inventors: Luc Gilles Charron, Toronto (CA); Thanh Vinh Vuong, Toronto (CA)

(*) Notice: Subject to any disclaimer, the term of this patent is extended or adjusted under 35 U.S.C. 154(b) by 14 days.

(21) Appl. No.: 15/894,189

(22) Filed: Feb. 12, 2018

(65) Prior Publication Data

US 2018/0228555 A1 Aug. 16, 2018

(51) Int. Cl.
*A61B 34/00* (2016.01)
*A61B 90/00* (2016.01)
*G06F 3/01* (2006.01)

(52) U.S. Cl.
CPC ............ *A61B 34/25* (2016.02); *A61B 90/361* (2016.02); *A61B 90/37* (2016.02); *G06F 3/012* (2013.01); *A61B 2090/365* (2016.02)

(58) Field of Classification Search
CPC .......... A61B 34/25; A61B 34/20; A61B 1/05; A61B 90/37; A61B 90/361; A61B 5/743; A61B 5/0215; A61B 5/02014; A61B 5/0066; A61B 2090/365; A61B 2034/2055; G06T 7/70; G06T 11/60; G06T 2207/30021; G06F 3/012
USPC ........................................................ 348/77
See application file for complete search history.

(56) References Cited

U.S. PATENT DOCUMENTS

| 2013/0009993 | A1* | 1/2013 | Horseman | G16H 40/63 |
| | | | | 345/633 |
| 2014/0055489 | A1* | 2/2014 | Itkowitz | G06T 11/40 |
| | | | | 345/633 |
| 2016/0267717 | A1* | 9/2016 | Bar-Zeev | G02B 27/017 |
| 2017/0181808 | A1* | 6/2017 | Panescu | A61B 34/32 |
| 2018/0168741 | A1* | 6/2018 | Swayze | G06K 9/346 |

OTHER PUBLICATIONS

Koreeda et al., "Virtually transparent surgical instruments in endoscopic surgery with augmentation of obscured regions", International journal of computer assisted radiology and surgery, Oct. 2016 (1927-36), 1861-6429.
Examination report from corresponding CA application [CA2958163] dated Feb. 16, 2018.

* cited by examiner

*Primary Examiner* — Allen C Wong (57) ABSTRACT

A system for assisting a surgeon to perform an operation on a patient where surgeon employs a first surgical instrument that has a shaft and a tip. The system include a video capture device configured to capture real-time video data showing the first surgical instrument while the first surgical instrument is being used by the surgeon to perform the operation. The system also includes a display device and a computer processor. The computer processor is configured to receive real-time video data from the video capture device as a sequence of digital image frames and, for each image frame, analyze the image frame to determine the location in the image frame of the shaft of the first surgical instrument, process the image frame to overlay received overlay information on the shaft of the first surgical instrument as it appears in the image frame, and display the processed image frame on the display device.

14 Claims, 8 Drawing Sheets

DIGITALLY ENHANCED SURGICAL INSTRUMENTS

TECHNICAL FIELD

The subject matter of the present disclosure generally relates to the field of systems to assist in surgery. More particularly, the subject matter of the present disclosure technically relates to systems for use in surgery that present to the surgeon virtually augmented views of the portion of a patient being operated on and surgical instruments being used to perform the surgery.

BACKGROUND

In performing surgery a surgeon employs surgical instruments that generally have a shaft and a tip. The tip may be, for example, a blade for cutting tissue of a patient, such as brain tissue. The shaft connects the tip to a portion that is held by the surgeon in the surgeon's hand and via which the surgeon can manipulate the instrument so that the tip cuts, or otherwise manipulates, contacts or is proximate to, tissue. The shaft of the instrument has thickness and the shaft thereby blocks the view of the surgeon of a portion of the patient's body tissues between the tip of the instrument and the portion of the instrument held by the patient.

It is often important for the surgeon to obtain measurements related to the operation in real-time during surgery, such as the patient's blood pressure and heart rate. In some systems a camera may track the instrument and calculate the distance between the tip of the instrument and the patient's tissue. Such information may be displayed to the surgeon on a computer display screen. However, this requires that the surgeon significantly change his focus to view the information and then change it again back to the tissue being operated on. Such changes are undesirable because they may be detrimental to optimal performance of delicate surgery, such as surgery performed on the brain. It would be preferable for the surgeon to not have to significantly change his or her focus repeatedly during the surgery.

SUMMARY

The invention described herein provides a system for assisting a surgeon to perform an operation on a patient employing a first surgical instrument. The first surgical instrument has a shaft. The system includes a video capture device, a display device and the computer processor. The video capture device is configured to capture real-time video data showing the first surgical instrument while the first surgical instrument is being used by the surgeon to perform the operation. The computer processor is configured to receive from the video capture device the real-time video data and to receive overlay information. The real-time video data consists of a sequence of digital image frames that are processed by the computer processor. For each image frame, the computer processor first analyzes the image frame to determine the location in the image frame of the shaft of the first surgical instrument. The computer processor then processes the image frame to overlay the overlay information on the shaft of the first surgical instrument as it appears in the image frame and displays the processed image frame on the display device.

Each processed image frame is preferably produced and displayed less than 0.05 seconds after the corresponding image frame was captured by the video capture device.

The overlay information may include information that varies over time and updated overlay information may be received by the computer processor in real-time, and for each image frame the updated overlay information may be overlaid on the shaft of the first surgical instrument as it appears in the image frame as the operation is being performed. The overlay information may include physiological information about the patient representing the state of the patient or a portion of the patient at the time the image frame was captured. The overlay information may include, for example, the patient's blood pressure or the patient's pulse rate. The overlay information may include information relating to a portion of the patient being operated on using the first surgical instrument, such as an estimate of thickness of tissue or thickness of an aneurysm wall proximate to the first surgical instrument in the portion of the patient being operated on. The thickness of tissue or the thickness of an aneurysm wall proximate to the first surgical instrument may be estimated from optical coherence tomography imagery of the portion of the patient being operated on.

The first surgical instrument may have a tip connected to the shaft. The system may also include a tracking subsystem configured to track the location of the first surgical instrument, and the overlay information may include the distance between the tip of the first surgical instrument and the patient as determined from information received from the tracking subsystem.

The overlay information may include information about the patient obtained before the operation commenced.

The overlay information may include text and for each image frame the text may be overlaid on the shaft of the first surgical instrument as it appears in the image frame so that the text is oriented in the same manner relative to the shaft of the first surgical instrument in each image frame. The text may include a string comprising N characters in a sequence, N being an integer greater than one, and for each position, i, in the sequence, i ranging from 1 to N, the i'th character of the string may be overlaid in the same location relative to the shaft of the first surgical instrument in each image frame.

During the operation the surgeon manipulates the first surgical instrument and may also manipulate a second surgical instrument which has a tip. The overlay information may include a representation of a button that is overlaid on a portion of the shaft of the first surgical instrument in the processed image frames. The computer processor may then be further configured to analyze the image frame to determine the location in the image frame of the tip of the second surgical instrument, determine whether the tip of the second surgical instrument is proximate to the portion of the shaft of the first surgical instrument on which the representation of a button is overlaid, and when the tip of the second surgical instrument is proximate to the portion of the shaft of the first surgical instrument on which the representation of a button is overlaid, then the computer processor may then perform an action. The system may also include a tracking subsystem configured to track the locations of the first surgical instrument and the second surgical instrument, and information received from the tracking subsystem may be used to determine if the tip of the second surgical instrument is proximate to the portion of the shaft of the first surgical instrument on which the representation of a button is overlaid. The action may, for example, include zooming the processed image frames prior to display on the display device. The action may include overlaying particular patient information on a portion of the shaft of the first surgical instrument. The overlay information comprises representations of multiple buttons, where each button corresponds to a different action.

The invention also provides a system for assisting a surgeon to perform a medical procedure on a patient, where the surgeon employs a first surgical instrument that has a shaft. The system includes a head-mounted augmented reality display device worn by the surgeon, where the display device is configured to display information overlaid on the field of view of the surgeon at a specified location. The system also includes a video capture device configured to capture real-time video data showing the field of view of the surgeon including the first surgical instrument while the first surgical instrument is being used by the surgeon to perform the procedure and a computer processor configured to analyze video received from the capture device the real-time video data, which is a sequence of digital image frames. The system receives overlay information and, for each image frame, analyzes the image frame to determine the location in the image frame of the shaft of the first surgical instrument and then displays the overlay information on the display device over the location of the first surgical instrument.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Figure 7:
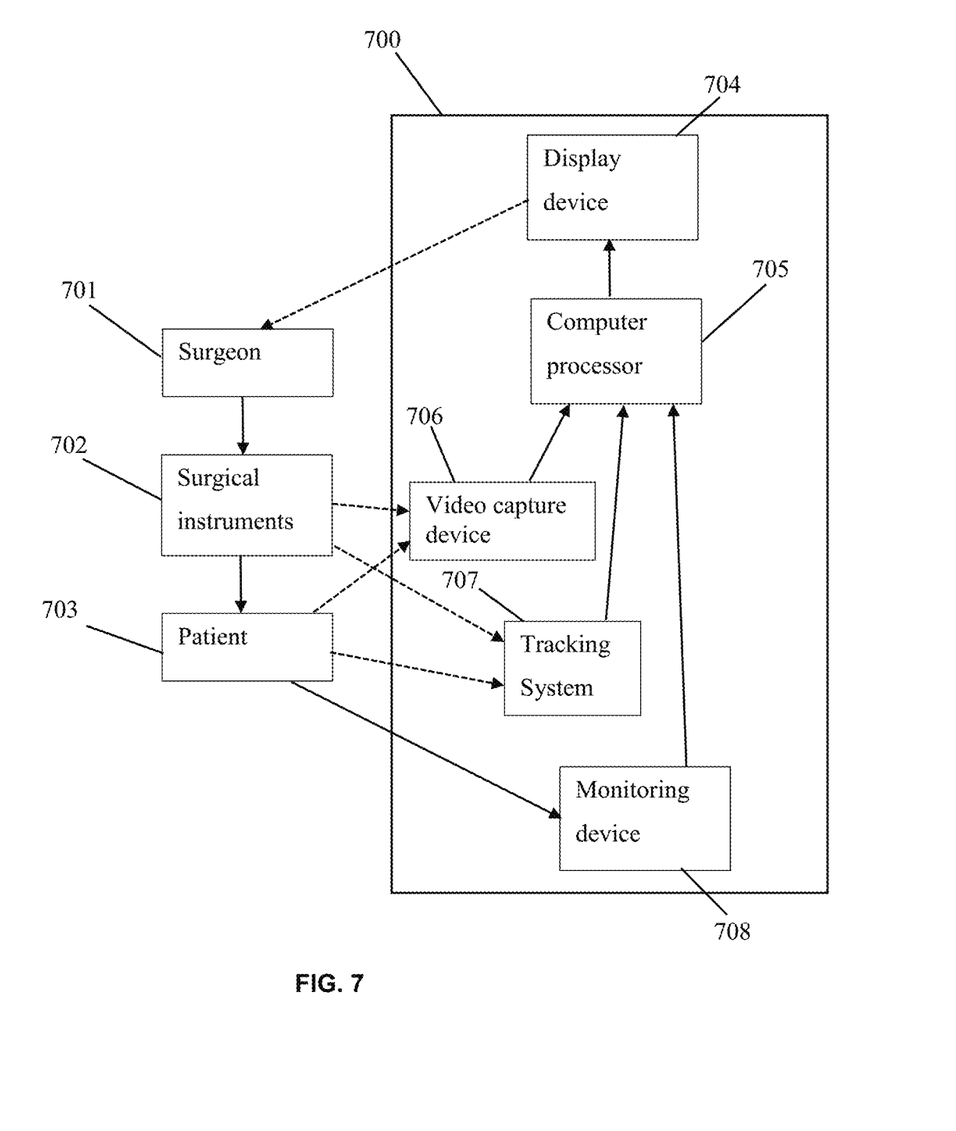
FIG. 7 shows the main elements of an exemplary system being used by a surgeon during an operation on a patient. Dashed lines indicate visual information such as reflected light.

FIG. 7 depicts the components of an exemplary embodiment of a system 700 for assisting a surgeon 701 to perform an operation on a patient 703 using one or more surgical instruments 702. The system 700 includes a display device 704, such as a display screen or head-mounted display, which presents processed video produced by and received in real-time from a computer processor 705 to the surgeon 701. The system 700 includes a video capture device 706 configured to have a field of view that includes the portion of the patient 703 being operated on (the operative region) and portions of the surgical instruments 702. An optional tracking system 707 is included in the system 700 for tracking the locations of the surgical instruments 702.

The video capture device 706 may be a camera, a surgical microscope, a videoscope or an exoscope that captures digital video data in real-time and has an interface to transmit the video to a computer processor 705 in real-time. The video capture device 706 has at least one lens for receiving light from the operative region. The operative region may be, for example, a portion of the patient's brain where a craniotomy has been performed to expose a portion of the brain. Portions of the surgical instruments 702 also appear in the field of view over the operative region as the operation is being performed.

Figure 8:
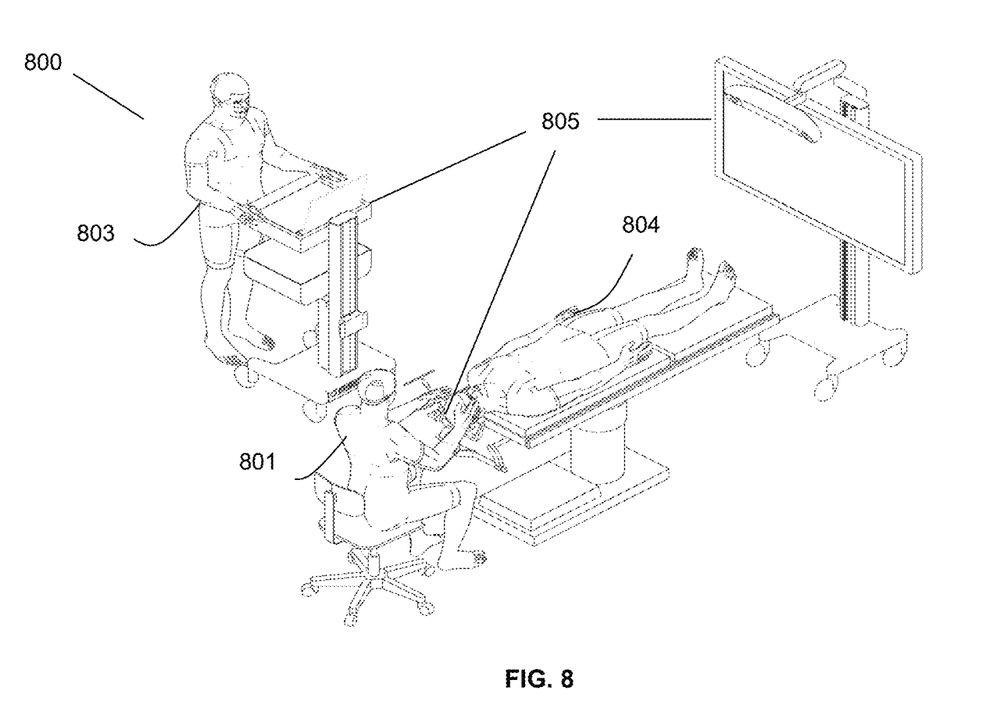
FIG. 8 depicts an exemplary navigation system environment.

Referring to FIG. 8, an exemplary navigation system environment 800 is shown. As shown in to FIG. 8, surgeon 801 conducts a surgery on a patient 802 in an operating room (OR) environment. A medical navigation system 805 comprising an equipment tower, tracking system, displays and tracked instruments assist the surgeon 801 during his procedure. An operator 803 is also present to operate, control and provide assistance for the medical navigation system 805. A detailed description of a surgical navigation system is outlined in international application PCT/CA2014/050270, entitled "SYSTEMS AND METHODS FOR NAVIGATION AND SIMULATION OF MINIMALLY INVASIVE THERAPY", which claims priority to U.S. Provisional Patent Application Ser. Nos. 61/800,155 and 61/924,993, which are all hereby incorporated by reference in their entirety.

Figure 1:
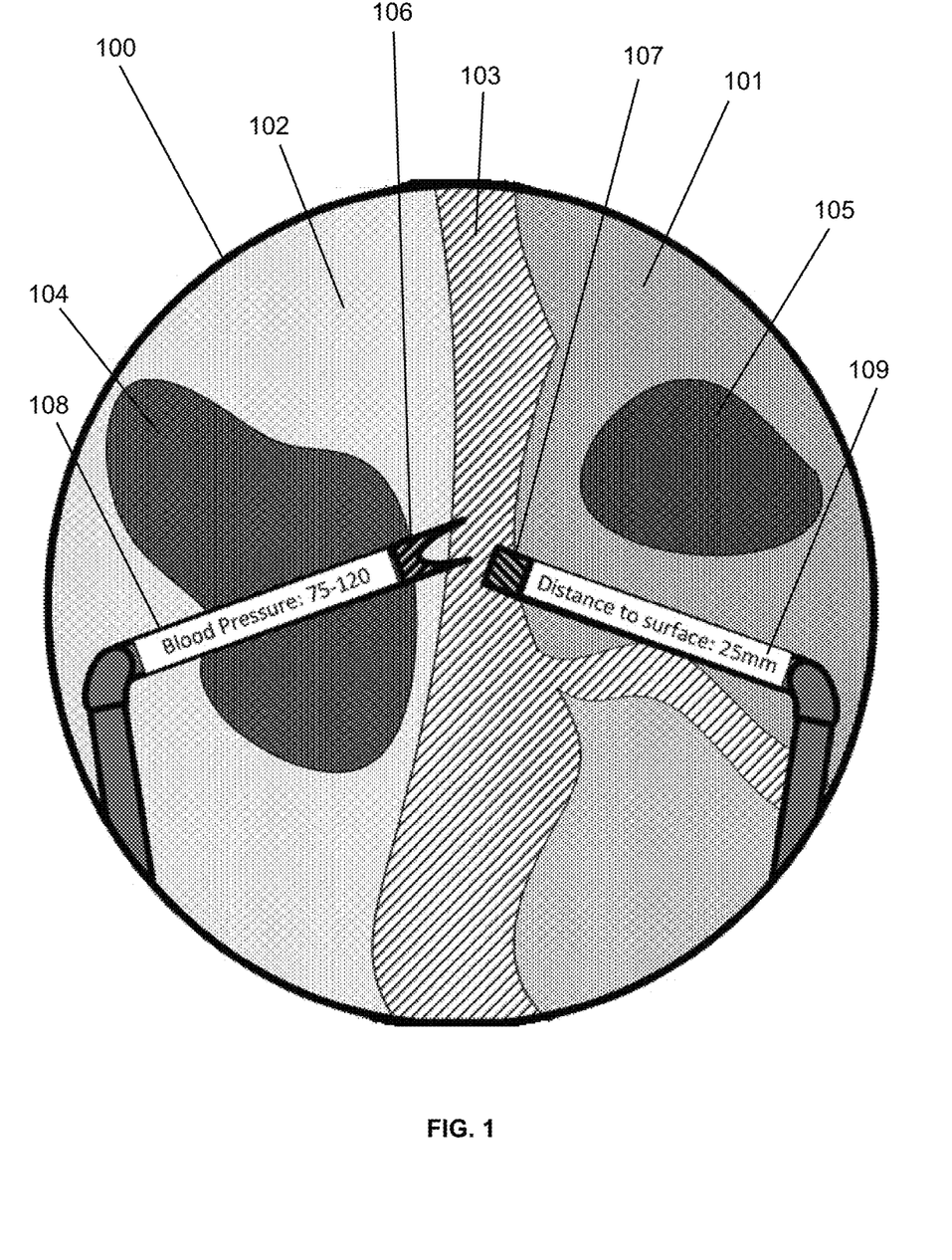
FIG. 1 is a schematic representation of a processed frame of video data showing an operative region of a patient's brain and showing first and second surgical instruments being used to perform surgery on the patient.

FIG. 1 depicts a video frame of a processed video data of an operative region, showing first and second surgical instruments being used to perform surgery on the patient. The video data frame has been processed by the computer processor 705, which is configured, preferably via software, to overlay information on the shafts 108, 109 of the surgical instruments as seen in each video frame in real-time.

FIG. 1 shows, in the operative region 100, healthy tissue 101, 102, vasculature 103 and two lesions 104, 105. The operation may involve, for example, removing the lesions. The first surgical instrument, depicted as surgical scissors, has a shaft 108 and a tip 106. In general, the tip of each surgical instrument is the portion of the instrument that contacts the patient's tissue or otherwise interacts with the patient's tissue, such as a cutting tip that is used by the surgeon to cut the patient's tissue, such as scissors 106 or a scalpel blade. It is generally critical that the tip be visible in the processed image frames, without any information being overlaid on the tip. The second surgical instrument, depicted as a suction device, also has a shaft 109 and a tip 107. The surgeon holds and manipulates the surgical instruments by holding each instrument in one hand. The portion of the instruments held by the surgeon (not show in the figures) may be referred to as a handle, which is rigidly connected to the proximate end of the shaft, or integrally formed with the shaft. The tip is rigidly attached to the distal end of the shaft or integrally formed with the shaft.

Video data is captured by the video capture device 706 for example, at a 60 Hz frame rate with a resolution of 1920× 1080 pixels, or other suitable rate and resolution. The video capture device 706 has a low latency analog to digital converter that converts the image viewed through the lens of the video capture device 706 to frames of digital video data in real-time. The digital video data is transmitted in real-time via an electronic interface to the computer processor 705 with low latency. For example, each processed image frame may be produced and displayed in preferably less than 0.1 seconds, or more preferably less than 0.05 seconds or 0.02 seconds, after the corresponding image frame was captured by the video capture device 706.

Normally, as the surgeon manipulates the instruments, the surgeon would see the shafts of the instruments such that they block the surgeon's view of a portion of the patient's body tissue in the operative region 100. Neurosurgery often deals with the problem of operating in very confined, and very small areas in order to avoid disrupting the brain. This leads to a very small field of view. The instruments used during surgeries will often get in the way of the surgeon's field of view which renders surgery much more challenging. The instruments themselves can become a source of distraction and frustration.

In the present system, the computer processor 705 receives overlay information and processes the video frames to overlay the overlay information on the shafts 108, 109 of the surgical instruments 702 as shown, for example, in FIGS. 1-5. Such an approach effectively increases the information the surgeon 701 can visualize since the view of the shafts of the instruments 702 alone provides no useful information to the surgeon 701 while taking up some of the field of view. By overlaying information on the shaft of an instrument, it is meant that the overlaid information only occupies a portion of the image that was previously occupied by a portion of the shaft of the instrument. The overlaid information does not spill over onto other portions of the image containing anything other than a portion of the shaft of the shaft of the instrument.

The computer processor 705 is configured to identify the shafts of the surgical instruments 702 in each video data frame, for example by using a known image segmentation algorithm. In some embodiments this may be facilitated by having the shaft portions of the surgical instruments 702 wrapped in a material with some uniform highly differentiated colour (e.g., fluorescent blue or green), which acts like a "green screen". Other known machine vision approaches may alternatively be employed. Having identified the locations in the frame of the shafts, the computer processor 705 identifies a suitable portion of each shaft over which to overlay information and then processes the image frame to digitally overlay the information on the identified portion of each shaft. The information is preferably overlaid in an orientation relative to the shafts that is constant across frames so that it appears to move as if the information were actually inscribed on the shaft as the instrument is moved. In other embodiments the information may be overlaid to optimize readability, while in yet further embodiments the information may be overlaid in a manner to optimize both readability and spatial persistence.

The overlay information may be obtained in real-time, or near real-time, from a monitoring device 708 that is continuously monitoring the patient. For such information, the information may be updated, and potentially change, as frequently as every digital image frame, although physical measurements generally measured at a lower rate and change at a significantly lower rate. For example, in FIGS. 1 and 2 the patient's blood pressure is part of the overlay information that has been overlaid on the shaft 108 of the first instrument. In FIG. 1, the blood pressure is 75-120 (diastolic-systolic) but in FIG. 2, captured at a different time, the overlaid blood pressure is 84-125. Such monitored overlay information is preferably transmitted by monitoring devices 708 in real-time with low latency so that the values shown overlaid on the instrument reflect the current values when the surgeon 701 views the processed image frames. The blood pressure reading may, for example, be updated every 10 seconds although the values overlaid on the instrument will only change when the updated value is different from the previous value.

Other information directly reflecting the state of the operation may also be obtained and overlaid on the instruments. For example, the second surgical instrument in FIGS. 1 and 2 has overlaid on its shaft 109 a measurement of the distance of the instrument to the surface of the patient, which changes as the surgeon 701 manipulates the instrument. This may be, for example, the minimum distance from the distal end (i.e. the end of the tool furthest from the surgeon's hands, which is normally an end of the tip) to the surface of the patient's body. This information may be provided by the tracking system in real-time with low latency or calculated by the computer processor 705 based on information received from the tracking system 707 in combination with information extracted by analyzing image frames. Information from the tracking system 707 is transmitted to the computer processor 705 via an electronic interface.

Overlay information may also include non-real-time information such as information about the patient obtained before the operation commenced. For example, previously measured information about a tumor involved in the operation may be overlaid. Such information may be obtained by the computer processor 705 from, for example, electronic databases stored in a storage device attached to the system 700 or accessible over an electronic network.

The surgeon may be able to change the type of overlay information displayed, for example via a voice recognition module that instructs the computer processor 705 to change the overlay information being shown on one of the instruments to a different type of overlay information as indicated by the surgeon's voice commands.

Figure 2:
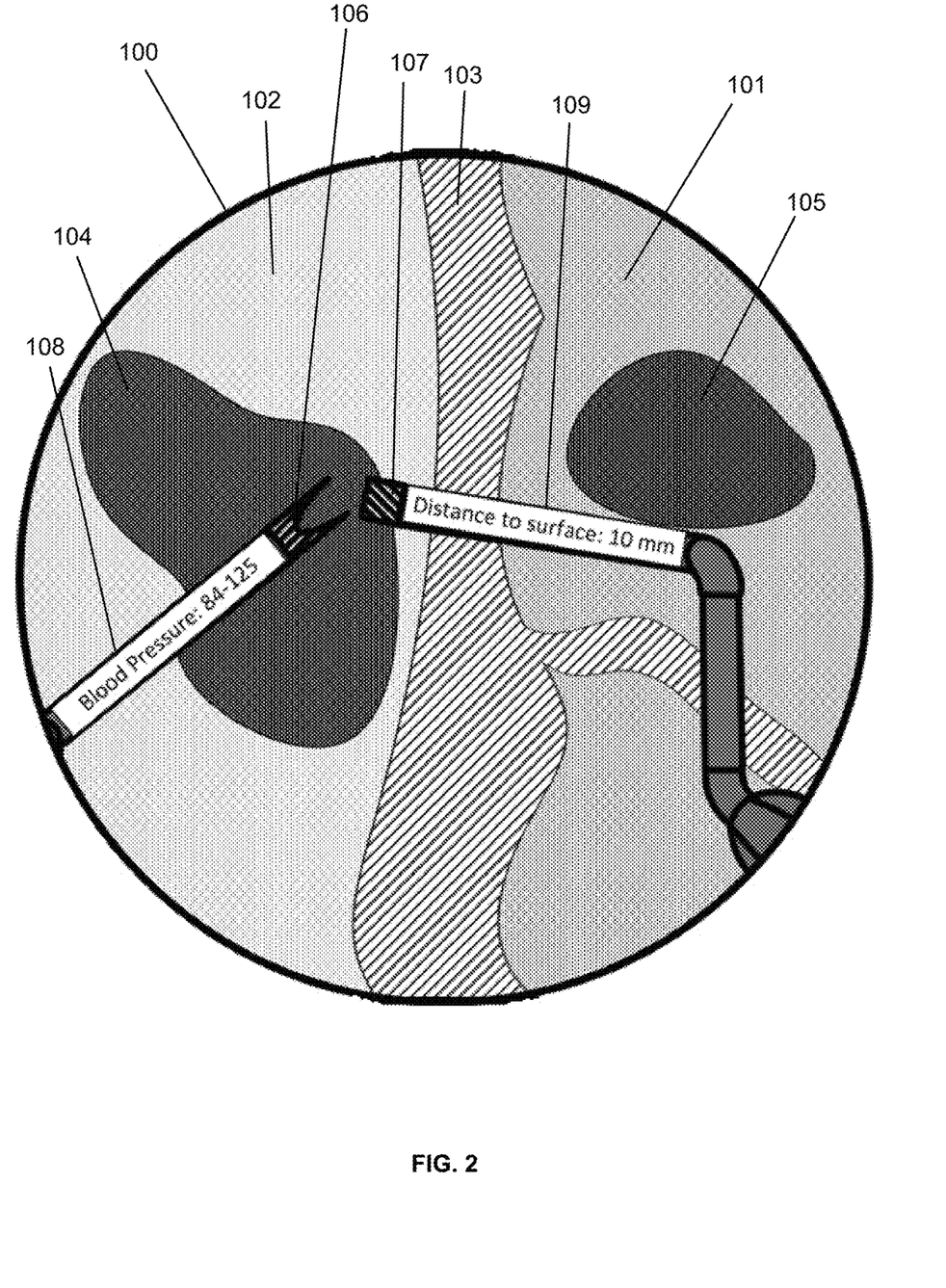
FIG. 2 is a schematic representation of a processed frame of video data showing the operative region of FIG. 1 showing the first and second surgical instruments of FIG. 1 in a different position.

As shown in FIGS. 1 and 2, it is preferred that when the overlay information includes text, the text is aligned along the length of a portion of the shaft so that the text is oriented in the same manner relative to the shaft of the surgical instrument in each image frame, as shown in FIGS. 1 and 2. The text is preferably oriented so that the text never appears upside down to the surgeon, which in some instances may require flipping the orientation of the overlaid text by 180 degrees as the orientation of the instruments changes (e.g. an instrument as shown in the figures is rotated though an orientation where the shaft is parallel to the sides of the drawing sheets). The absolute location and orientation of the overlaid information (e.g. relative to the operative region) therefore may change frequently or nearly continuously, whereas the location and orientation of the overlaid information relative to the surgical instruments is fixed from frame to frame unless there are instances when the orientation is flipped.

Examples of information that may be overlaid include:
Physiological patient information (pulse, O2, time, timers);

Physical measurements (e.g., aneurysm wall thickness as measured with optical coherence tomography (OCT)) or distance to target (from navigation information;

Brain activity measurements;

Proximity warnings and distance information to target (information relayed using navigation and tracked tools;

Additional sensing information measurements (optical signals (fluorescence, Raman, absorbance), electrical signals (impedance, current, etc.) from smart tools or sensing package integrated with instruments (such as suction, bi-polar, etc.);

Instrument setting status (e.g., bi-polar cauterizing or cutting setting)

Imaging information (tissue thickness, aneurysm wall thickness, etc.) via imaging modalities such as OCT;

Tissue properties (high lipid content, protein content, optical signals, such as fluorescence (from sensing packages attached to smart tools/instruments, etc.).

Surgical Guidance Information (distance to target, rotation to angle, depth of probe, deflection of probe etc.; and Spatial Anatomical information, for example as derived from the tracking system (such as indicating that vasculature is in the vicinity of the tip of the instrument, or vicinity too nerve fibers, or name of white matter tract such as the superior longitudinal fasciculus (SLF) or optic tract, or in the case of spine surgery the spinal cord direction).

Figure 3:
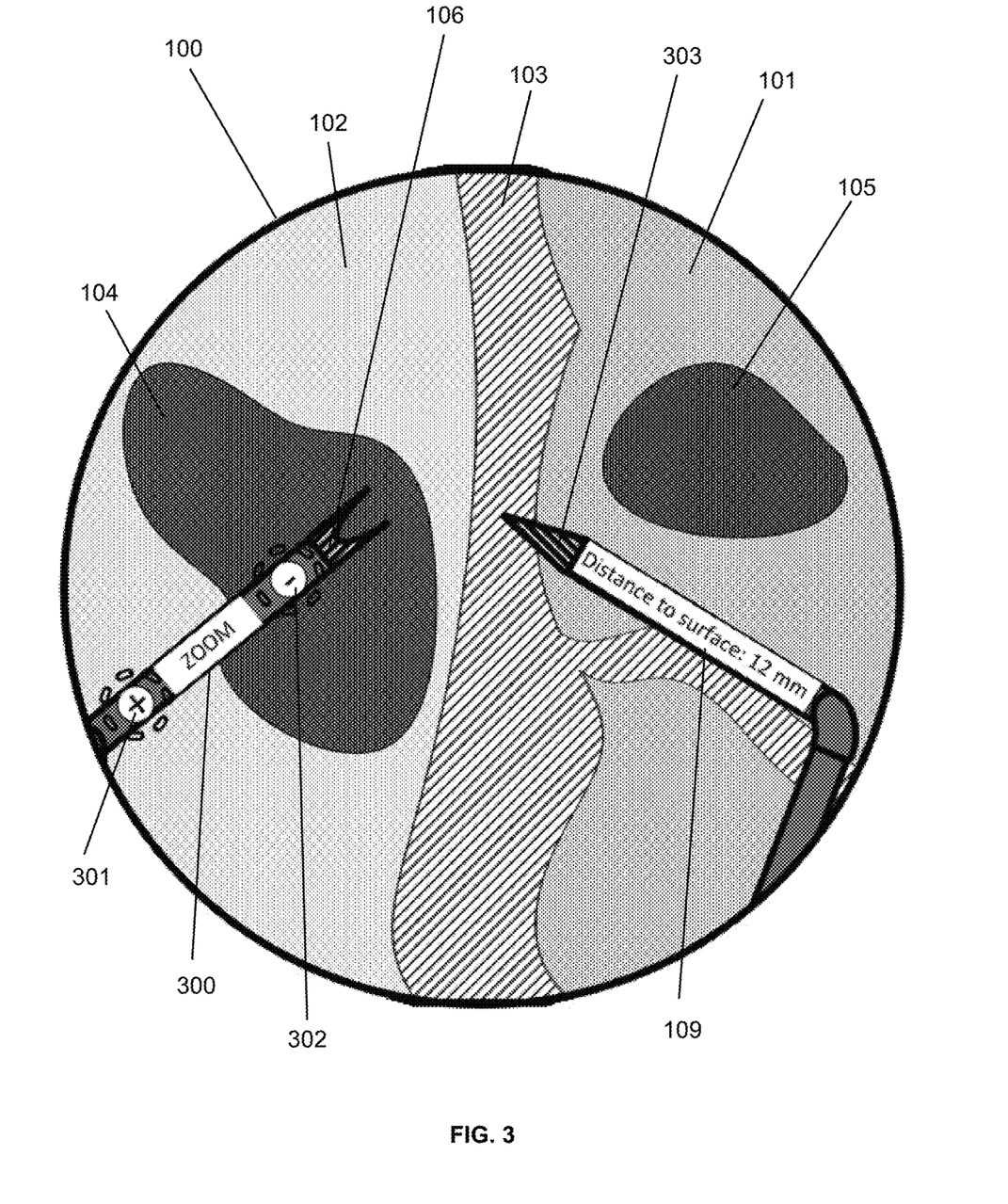
FIG. 3 is a schematic representation of a processed frame of video data showing an operative region of a patient's brain and showing first and third surgical instruments being used to perform surgery on the patient.
Figure 4:
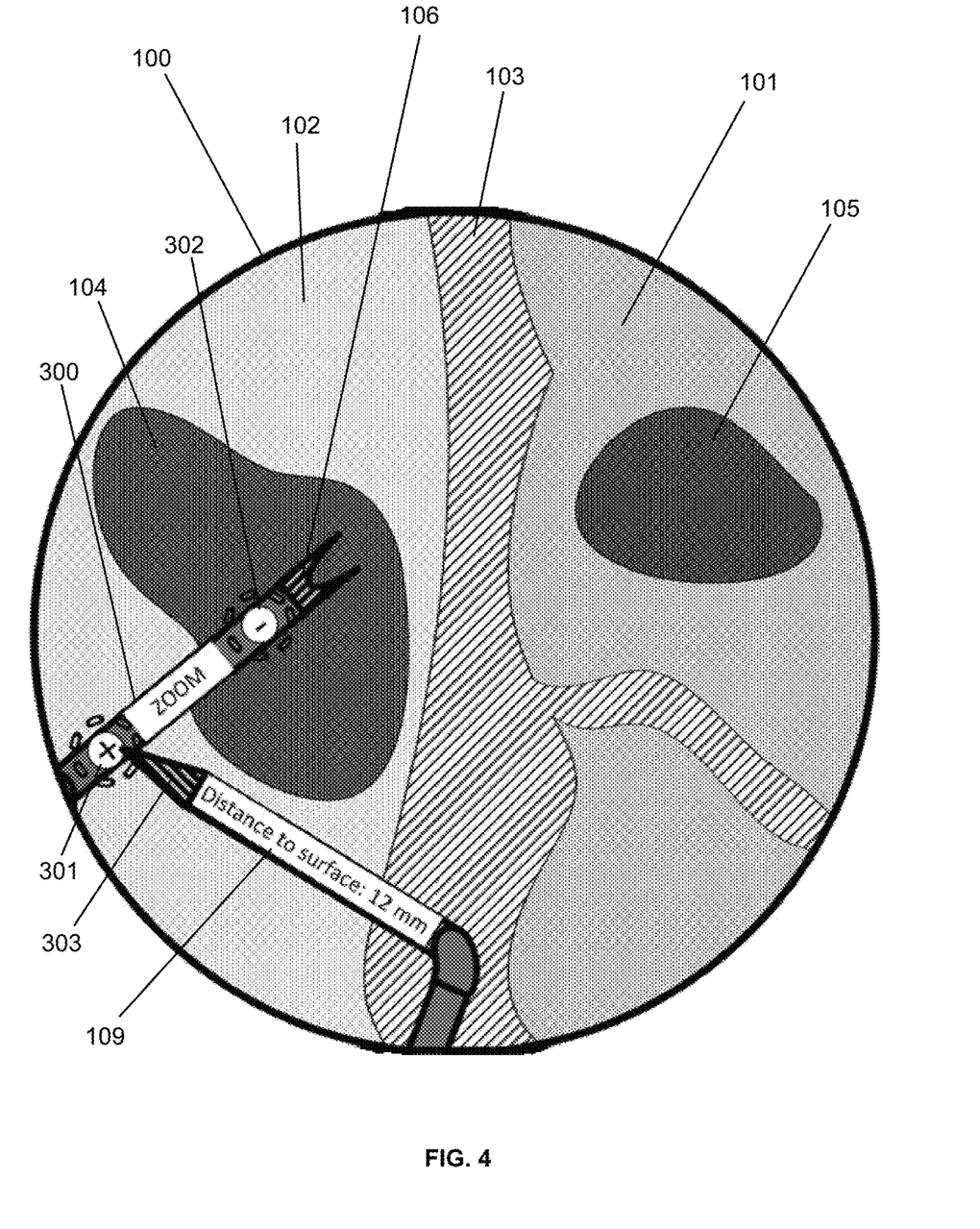
FIG. 4 is a schematic representation of a processed frame of video data showing the operative region of FIG. 3 and showing first and third surgical instruments where the tip of the third instrument is touching a virtual button displayed on the shaft of the first instrument.
Figure 5:
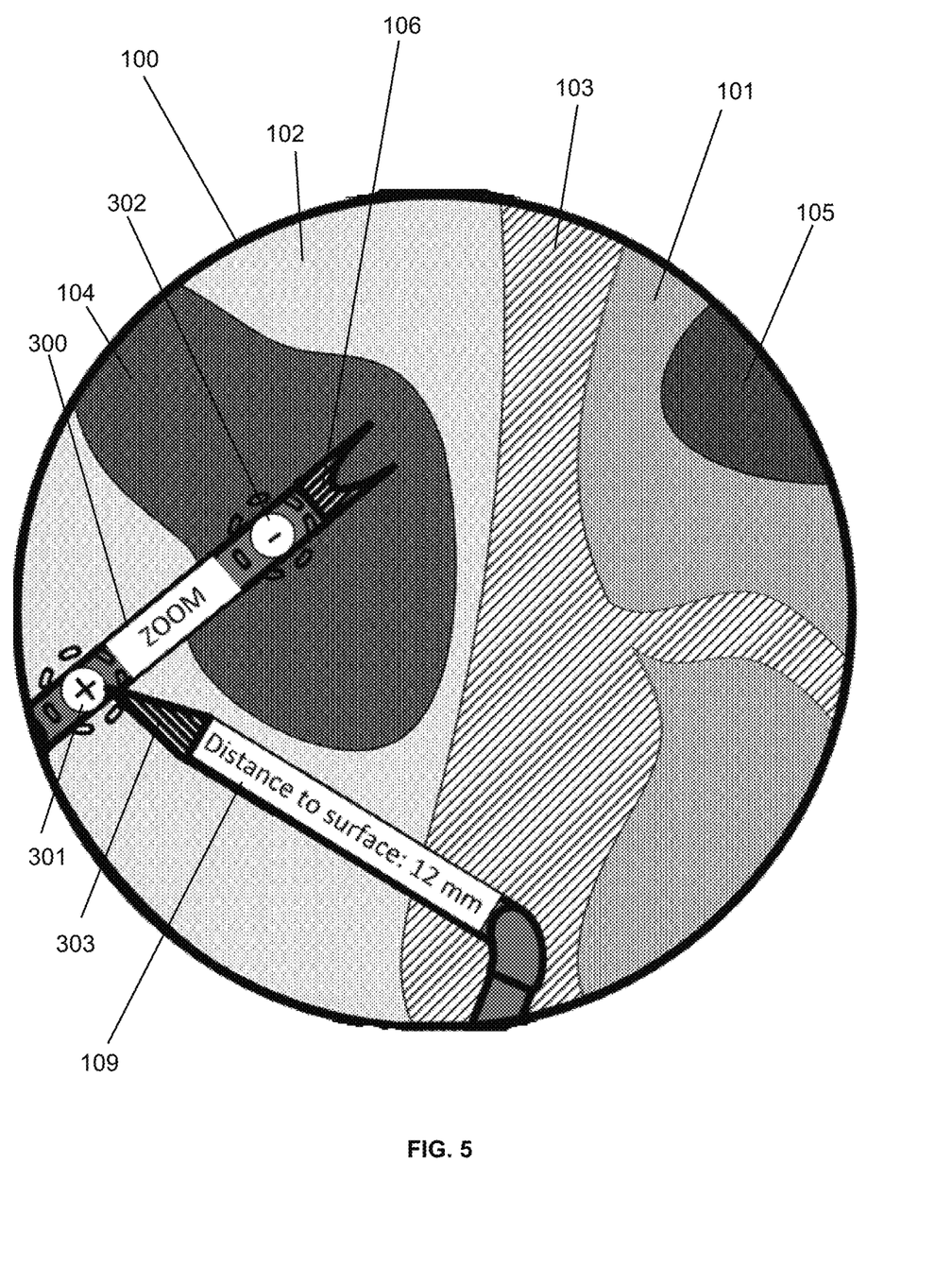
FIG. 5 is a schematic representation of the view of FIG. 4 where the view has been zoomed.

Overlay information does not necessarily contain text or consist entirely of text. For example, FIGS. 3-5 show an example where the overlay information includes representations of two buttons, which may be referred to a virtual buttons, that are overlaid on a portion of the shaft 300. One button 301 includes a "+" and the other 302 includes a "−" with the text "ZOOM" overlaid on the shaft 300 between the buttons. In general, such virtual buttons can be used to cause a particular action to be performed by the computer processor 705. Such actions typically involve the computer processor 705 altering the manner in which the image frames are being processed, for example to change the type of overlay information being overlaid on one of the instruments or to make overall changes to the displayed video images.

In the example of FIGS. 3-5, the virtual buttons are used to control zooming of the displayed image. In FIG. 4, the surgeon has moved the second instrument so that the tip 303 of the second instrument contacts, or is brought proximate to, the "+" virtual button. In this example, the prescribed action is to zoom in by a predefined amount, resulting in the display shown in FIG. 5. The computer processor 705 may be programmed to zoom the images continuously by small pre-determined amounts from frame to frame as long as the tip 303 of the second instrument remains in contact with, or proximate to, the "+" virtual button. The surgeon may later zoom out by bringing the tip 303 of the second instrument in contact with, or proximate to, the "−" virtual button.

The overlay information may be overlaid on the entire visible shaft of an instrument, rather than on just a portion of the visible shaft of the instrument. This may be useful, for example, to clearly distinguish the shaft of the instrument from the patient's tissue. In general though, lines defining/delimiting the boundary of the shaft of the instrument, such as those shown in FIG. 5, are included in the processed image. Rather than, or in addition to, textual information, the overly information may include unique shapes, patterns or texture that differentiates the shaft of the instrument from the background image/video feed.

Figure 6:
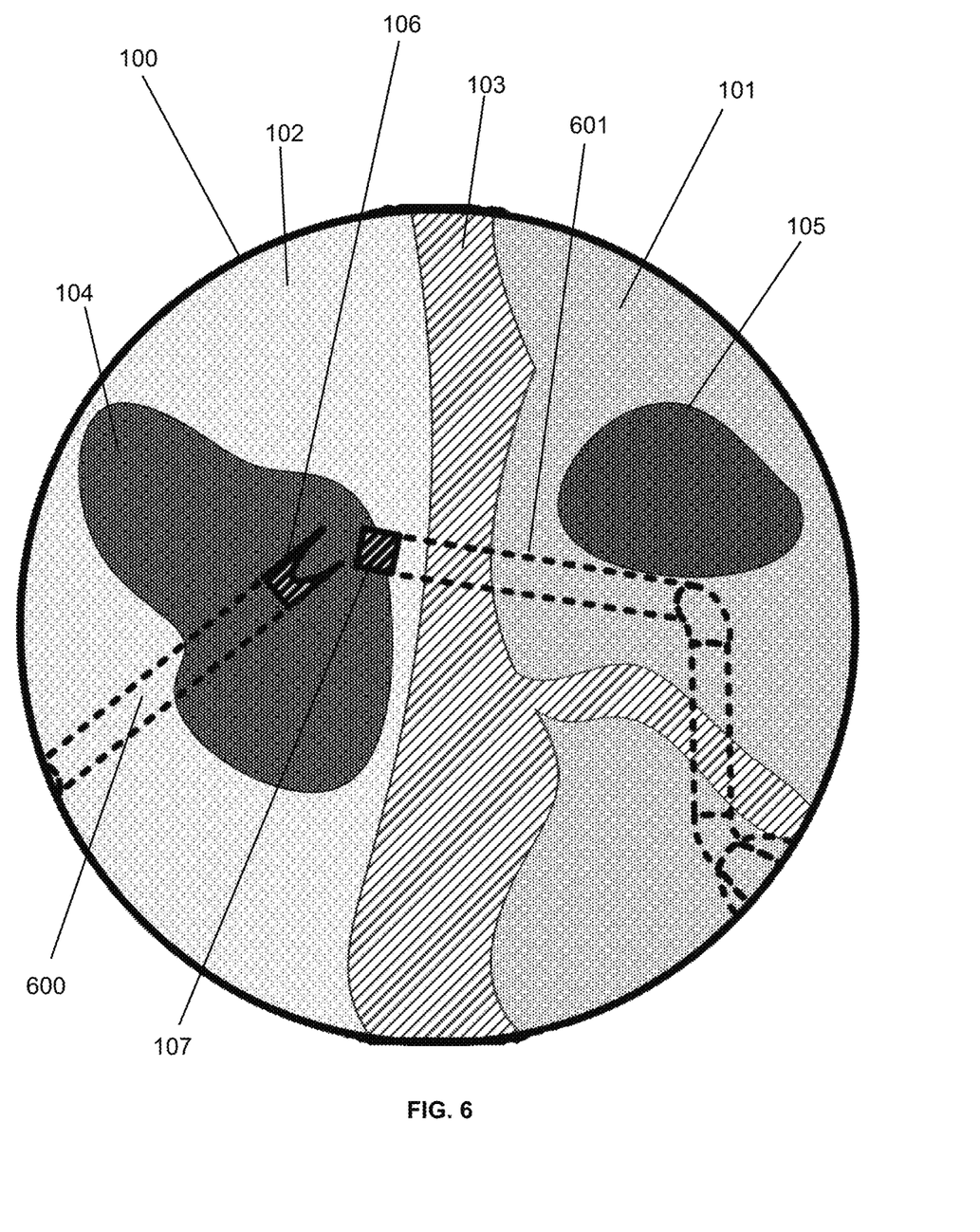
FIG. 6 is a schematic representation of a processed frame of video data showing an operative region of a patient's brain and showing first and second surgical instruments being used to perform surgery on the patient where the shafts of the first and second surgical instruments have been effectively rendered transparent.

In other embodiments, rather than overlay information, previously recorded image data may be overlaid on surgical instruments. FIG. 6 shows a view where the shafts 600, 601 of the surgical instruments have image data overlaid on them, rendering them apparently transparent, although preferably the outer edges of the shafts of the instruments are indicated in the view, such as with dotted lines as shown in FIG. 6. In such embodiments, the previous video data received from the data capture device is stored by the system so that for a given new video frame with the instrument shafts in particular locations, the computer processor can search back through the stored video data to find the most recent stored video frames where all or some of the current locations of the shafts were not obstructed by the instruments. The current locations of the shafts may be determined by a known segmentation algorithm. Since the patient's tissue remains in a relatively fixed location in the operative region, the processor can analyze the same location in prior stored image frames to determine whether the location was obstructed or if the view of the patient's tissue in that location is available, in whole or in part. The distinction obstructed and non-obstructed portions between is readily ascertained, for example, by the use of a uniform highly differentiated colour on the shafts of the instruments or through using machine vision methods, as discussed above. The system may also store the previously determined locations of the shafts of the instruments along with each frame of stored video data so that no further processing of the stored video frames needs to be done to determine which obstructed portions of the current frame are visible in a stored frame and which are obstructed.

Because the instruments are generally constantly moving in the surgical field, the parts of the patient masked by the instruments can be constantly refreshed and projected digitally over the shafts of the instruments. The overlaid image data for the current image frame with an instrument shaft obstructing the view of a particular portion is preferably selected from the most recent previous image frame(s) in which the image shaft did not obstruct the view of that portion of the patient. The corresponding image data can be extracted from multiple such previous frames and mosaicked (i.e. stitched together) to produce overlay imagery that provides the most recent available view of each portion of the patient for which the view is blocked by the instruments in the current frame. Alternatively, the image data from the most recent prior frame showing the complete obstructed region may be used. When the stored image data is overlaid on the shafts it creates the impression that the shafts are transparent. While any changes in the obstructed region occurring while the shaft is over the region obstructing the view of the region will not be immediately visible, this is generally not a problem as the instruments are normally moving frequently.

It should be noted that the previously stored image data was obtained with the video capture device and the operative region in the same location so that no geometric correction (e.g. warping) of the previously stored image data is required prior to overlaying the image data on the instrument shafts. This would not be the case, for example, if the overlaid image data were obtained from a second camera.

Optical tracking systems, which may be used in the medical procedure, track the position of a part of the instruments that are within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked. It should be noted that any embodiments provided herein which employ an optical tracking system may be extended to any relevant tracking system as are known in the art, and thus the examples provided below should not be taken to limit the scope of the invention as disclosed herein.

In other embodiments of the invention, rather than processing the image frames to overlay the overlay information on the shaft of the first surgical instrument as it appears in the image frames, the invention may employ a head-mounted augmented reality display device worn by the surgeon. In such embodiments, rather than process the image frames to insert the overlay information, the system need only control the augmented reality display device to cause it to display the overlay information on the display device over the location of the first surgical instrument. In such embodiments, the surgeon sees the patient's tissue directly, but with the overlay information positioned on top of the shaft of one or more surgical instruments in the surgeon's field of view.

It should be understood that the term "shaft" as used herein in respect of a surgical instrument includes all portions of a surgical instrument that a surgeon does not need to see during an operation (i.e. portions of the instrument the viewing of which provides no information to the surgeon necessary or useful for conducting the surgery beyond the location of the shaft). For an instrument such as a scalpel, the "shaft" may be the portion that would normally be referred to as the handle, but the concept of a shaft is not so limited. For example, where the surgical instrument is a flexible catheter hose, then the shaft may be the length of the hose. In some embodiments where the hands of the surgeon are in the field of view, those portions of the images may also be identified and overlaid with information.

Generally, a computer, computer system, computing device, client or server, as will be well understood by a person skilled in the art, includes one or more than one electronic computer processor, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. It is the express intent of the inventors that a "processor" does not include a human; rather it is limited to be an electronic device, or devices, that perform digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

Multiple computers (also referred to as computer systems, computing devices, clients and servers) may be networked via a computer network, which may also be referred to as an electronic network or an electronic communications network. When they are relatively close together the network may be a local area network (LAN), for example, using Ethernet. When they are remotely located, the network may be a wide area network (WAN), such as the internet, that computers may connect to via a modem, or they may connect to through a LAN that they are directly connected to.

Computer-readable memory, which may also be referred to as a computer-readable medium or a computer-readable storage medium, which terms have identical (equivalent) meanings herein, can include any one or a combination of non-transitory, tangible memory elements, such as random access memory (RAM), which may be DRAM, SRAM, SDRAM, etc., and nonvolatile memory elements, such as a ROM, PROM, FPROM, OTP NVM, EPROM, EEPROM, hard disk drive, solid state disk, magnetic tape, CDROM, DVD, etc.) Memory may employ electronic, magnetic, optical, and/or other technologies, but excludes transitory propagating signals so that all references to computer-readable memory exclude transitory propagating signals. Memory may be distributed such that at least two components are remote from one another, but are still all accessible by one or more processors. A nonvolatile computer-readable memory refers to a computer-readable memory (and equivalent terms) that can retain information stored in the memory when it is not powered. A computer-readable memory is a physical, tangible object that is a composition of matter. The storage of data, which may be computer instructions, or software, in a computer-readable memory physically transforms that computer-readable memory by physically modifying it to store the data or software that can later be read and used to cause a processor to perform the functions specified by the software or to otherwise make the data available for use by the processor. In the case of software, the executable instructions are thereby tangibly embodied on the computer-readable memory. It is the express intent of the inventor that in any claim to a computer-readable memory, the computer-readable memory, being a physical object that has been transformed to record the elements recited as being stored thereon, is an essential element of the claim.

Software may include one or more separate computer programs configured to provide a sequence, or a plurality of sequences, of instructions to one or more processors to cause the processors to perform computations, control other devices, receive input, send output, etc.

It is intended that the invention includes computer-readable memory containing any or all of the software described herein. In particular, the invention includes such software stored on non-volatile computer-readable memory that may be used to distribute or sell embodiments of the invention or parts thereof.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed. Unless expressly stated or otherwise clearly implied herein, the conjunction "or" as used in the specification and claims shall be interpreted as a non-exclusive "or" so that "X or Y" is true when X is true, when Y is true, and when both X and Y are true, and "X or Y" is false only when both X and Y are false.

The abbreviation mm as used herein refers to millimetres (or in the US, "millimeters"). The abbreviation cm as used herein refers to centimeters (or in the US, "centimeters").

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed. Unless expressly stated or otherwise clearly implied herein, the conjunction "or" as used in the specification and claims shall be interpreted as a non-exclusive "or" so that "X or Y" is true when X is true, when Y is true, and when both X and Y are true, and "X or Y" is false only when both X and Y are false.

The words "comprises" and "comprising", when used in this specification and the claims, are to used to specify the presence of stated features, elements, integers, steps or components, and do not preclude, nor imply the necessity for, the presence or addition of one or more other features, elements, integers, steps, components or groups thereof.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art.

It should be understood that the above-described embodiments of the present invention, particularly, any "preferred" embodiments, are only examples of implementations, merely set forth for a clear understanding of the principles of the invention. Many variations and modifications may be made to the above-described embodiment(s) of the invention as will be evident to those skilled in the art. That is, persons skilled in the art will appreciate and understand that such modifications and variations are, or will be, possible to utilize and carry out the teachings of the invention described herein.

The scope of the claims that follow is not limited by the embodiments set forth in the description. The claims should be given the broadest purposive construction consistent with the description and figures as a whole.

What is claimed is:

1. A system for assisting a surgeon to perform an operation on a patient, the surgeon employing a first surgical instrument comprising a shaft, the system comprising:

a video capture device configured to capture real-time video data showing the first surgical instrument while the first surgical instrument is being used by the surgeon to perform the operation;
    a display device; and
    a computer processor configured to:
    receive from the video capture device the real-time video data comprising a sequence of digital image frames;
    receive overlay information; and
    for each image frame:
    analyze the image frame to determine the location in the image frame of the shaft of the first surgical instrument;
    process the image frame to overlay the overlay information on the shaft of the first surgical instrument as the first surgical instrument appears in the image frame;
    display the processed image frame on the display device; and
    a tracking subsystem configured to track the location of the first surgical instrument,
    wherein the overlay information comprises information that varies over time, wherein updated overlay information is received by the computer processor in real-time, wherein, for each image frame, the updated overlay information is overlaid on the shaft of the first surgical instrument as the first surgical instrument appears in the image frame while the operation is being performed, wherein the overlay information comprises physiological information about the patient, the physiological information representing the state of the patient or a portion of the patient at the time the image frame was captured, wherein the overlay information comprises information relating to a portion of the patient being operated on using the first surgical instrument, wherein the first surgical instrument further comprises a tip connected to the shaft, and wherein the overlay information comprises the distance between the tip of the first surgical instrument and the patient as determined from information received from the tracking subsystem.

2. The system of claim 1, wherein each processed image frame is produced and displayed less than 0.05 seconds after the corresponding image frame was captured by the video capture device.

3. The system of claim 1, wherein the overlay information comprises the patient's blood pressure or the patient's pulse rate.

4. The system of claim 1, wherein the overlay information comprises an estimate of thickness of tissue or thickness of an aneurysm wall proximate to the first surgical instrument in the portion of the patient being operated on.

5. The system of claim 4, wherein the thickness of tissue or the thickness of an aneurysm wall proximate to the first surgical instrument is estimated from optical coherence tomography imagery of the portion of the patient being operated on.

6. The system of claim 1, wherein the overlay information comprises information about the patient obtained before the operation commenced.

7. The system of claim 1, wherein the overlay information comprises text wherein, for each image frame the text is overlaid on the shaft of the first surgical instrument as the first surgical instrument appears in the image frame, and wherein the text is oriented in the same manner relative to the shaft of the first surgical instrument in each image frame.

8. The system of claim 7, wherein the text comprises a string comprising N characters in a sequence, N being an integer greater than one, and for each position, i, in the sequence, i ranging from 1 to N, the i'th character of the string is overlaid in the same location relative to the shaft of the first surgical instrument in each image frame.

9. The system of claim 1, wherein during the operation the surgeon manipulates the first surgical instrument and also manipulates a second surgical instrument comprising a tip, wherein the overlay information comprises a representation of a button that is overlaid on a portion of the shaft of the first surgical instrument in the processed image frames, and wherein the computer processor is further configured to:
- analyze the image frame to determine the location in the image frame of the tip of the second surgical instrument;
- determine whether the tip of the second surgical instrument is proximate to the portion of the shaft of the first surgical instrument on which the representation of a button is overlaid; and
- when the tip of the second surgical instrument is proximate to the portion of the shaft of the first surgical instrument on which the representation of a button is overlaid, then perform an action.

10. The system of claim 9 further comprising a tracking subsystem configured to track the locations of the first surgical instrument and the second surgical instrument, wherein information received from the tracking subsystem is used to determine if the tip of the second surgical instrument is proximate to the portion of the shaft of the first surgical instrument on which the representation of a button is overlaid.

11. The system of claim 9, wherein the action comprises zooming the processed image frames prior to display on the display device.

12. The system of claim 9, wherein the action comprises overlaying particular patient information on a portion of the shaft of the first surgical instrument.

13. The system of claim 9, wherein the overlay information comprises representations of a plurality of buttons, wherein each button corresponds to a different action.

14. A system for assisting a surgeon to perform a medical procedure, the surgeon employing a first surgical instrument comprising a shaft, the system comprising:
- a head-mounted augmented reality display device worn by the surgeon, the display device being configured to display information overlaid on the field of view of the surgeon at a specified location;
- a video capture device configured to capture real-time video data showing the field of view of the surgeon including the first surgical instrument while the first surgical instrument is being used by the surgeon to perform the procedure;
- a computer processor configured to:
  - receive from the video capture device the real-time video data comprising a sequence of digital image frames;
  - receive overlay information; and
  - for each image frame: analyze the image frame to determine the location in the image frame of the shaft of the first surgical instrument; and display the overlay information on the display device over the location of the first surgical instrument; and
- a tracking subsystem configured to track the location of the first surgical instrument,
wherein the overlay information comprises information that varies over time, wherein updated overlay information is received by the computer processor in real-time, wherein, for each image frame, the updated overlay information is overlaid on the shaft of the first surgical instrument as the first surgical instrument appears in the image frame while the operation is being performed, wherein the overlay information comprises physiological information about the patient, the physiological information representing the state of the patient or a portion of the patient at the time the image frame was captured, wherein the overlay information comprises information relating to a portion of the patient being operated on using the first surgical instrument, wherein the first surgical instrument further comprises a tip connected to the shaft, and wherein the overlay information comprises the distance between the tip of the first surgical instrument and the patient as determined from information received from the tracking subsystem.

* * * * *